(12) United States Patent
Kameshima et al.

(10) Patent No.: US 7,532,706 B2
(45) Date of Patent: May 12, 2009

(54) IMAGING APPARATUS, IMAGING SYSTEM, IMAGING METHOD, AND COMPUTER PROGRAM

(75) Inventors: Toshio Kameshima, Kumagaya (JP); Tadao Endo, Honjo (JP); Tomoyuki Yagi, Honjo (JP); Katsuro Takenaka, Kodama-gun (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/319,910

(22) Filed: Dec. 27, 2005

(65) Prior Publication Data

US 2006/0104417 A1 May 18, 2006

Related U.S. Application Data

(63) Continuation of application No. PCT/JP2005/014436, filed on Aug. 5, 2005.

(30) Foreign Application Priority Data

Aug. 6, 2004 (JP) ............................. 2004-231446
Aug. 4, 2005 (JP) ............................. 2005-226622

(51) Int. Cl.
*H05G 1/64* (2006.01)
*H05G 1/58* (2006.01)
*H03G 3/00* (2006.01)
*H01L 27/146* (2006.01)

(52) U.S. Cl. .................. 378/98; 378/116; 250/214 AG; 250/370.09

(58) Field of Classification Search .................. 378/91, 378/98, 98.8, 98.9, 114, 115, 116, 21, 19, 378/97, 207, 210; 382/131, 270, 271, 272, 382/273; 250/363.01, 363.02, 370.08, 370.09, 250/393, 214 AG, 363.07, 363.09, 370.01
See application file for complete search history.

(56) References Cited

U.S. PATENT DOCUMENTS 4,097,732 A * 6/1978 Krause et al. ................ 250/205
4,703,496 A * 10/1987 Meccariello et al. ........ 378/98.7

(Continued)

FOREIGN PATENT DOCUMENTS

EP 0881828 12/1998

(Continued)

OTHER PUBLICATIONS

Karim, et al., X-ray Detector with On-pixel Amplification for Large Area Diagnostic Medical Imaging, Aug. 2003, IEEE Proc.-Circuits Devices Syst., vol. 150, No. 4, pp. 267-273.*

(Continued)

*Primary Examiner*—Allen C. Ho
*Assistant Examiner*—Anastasia Midkiff
(74) *Attorney, Agent, or Firm*—Locke Lord Bissell & Liddell, LLP

(57) ABSTRACT

A correction process is performed using different gain correction signals (GSA, GSB) in accordance with radiographic modes (moving image radiographic mode/still image radiographic mode) set in an X-ray imaging apparatus, respectively. This makes it possible to acquire an image with decreased correction errors even when the X-ray imaging apparatus is configured using an imaging unit having different gain characteristics in the still image radiographic mode and moving image radiographic mode.

15 Claims, 15 Drawing Sheets

U.S. PATENT DOCUMENTS

| | | | |
|---|---|---|---|
| 4,910,592 A * | 3/1990 | Shroy et al. | 378/98.7 |
| 4,930,144 A * | 5/1990 | Plut et al. | 378/98.7 |
| 5,608,207 A * | 3/1997 | Allen et al. | 250/214 AG |
| 6,191,412 B1 * | 2/2001 | Afghahi | 250/214 AG |
| 6,333,963 B1 * | 12/2001 | Kaifu et al. | 378/98.2 |
| 6,350,985 B1 * | 2/2002 | Rodricks et al. | 250/252.1 |
| 6,393,098 B1 * | 5/2002 | Albagli | 378/98.2 |
| 6,731,783 B2 * | 5/2004 | Tsujii | 382/132 |
| 6,744,912 B2 * | 6/2004 | Colbeth et al. | 382/132 |
| 6,920,198 B2 * | 7/2005 | Xue et al. | 378/62 |
| 7,026,608 B2 * | 4/2006 | Hirai | 250/252.1 |
| 7,203,279 B2 * | 4/2007 | Fujii et al. | 378/116 |
| 7,227,926 B2 * | 6/2007 | Kameshima et al. | 378/98.9 |
| 7,312,856 B2 * | 12/2007 | Flockencier | 356/5.01 |
| 2003/0035509 A1 * | 2/2003 | Boehm et al. | 378/98.8 |
| 2003/0132391 A1 * | 7/2003 | Agano | 250/370.11 |
| 2004/0008813 A1 * | 1/2004 | Endo | 378/62 |
| 2004/0120452 A1 * | 6/2004 | Shapiro et al. | 378/19 |
| 2004/0218729 A1 * | 11/2004 | Xue et al. | 378/210 |
| 2005/0082491 A1 * | 4/2005 | Seppi et al. | 250/370.11 |
| 2005/0109927 A1 * | 5/2005 | Takenaka et al. | 250/252.1 |
| 2005/0263709 A1 * | 12/2005 | Watanabe et al. | 250/370.11 |

FOREIGN PATENT DOCUMENTS

| | | |
|---|---|---|
| JP | 02248889 A * | 10/1990 |
| JP | 10-327317 | 12/1998 |
| JP | 2002-305687 | 10/2002 |
| JP | 2003-24457 | 1/2003 |
| JP | 2003-244540 | 8/2003 |
| JP | 2004-15000 | 1/2004 |
| JP | 2004-23654 | 1/2004 |
| WO | WO 98/24059 | 6/1998 |

OTHER PUBLICATIONS

International Search Report dated Nov. 15, 2005.
Written Opinion by the International Search Authority concerning basic application PCT/JP2005/901136.
Full English translation of JP 2003-244540, published Aug. 29, 2003.

* cited by examiner

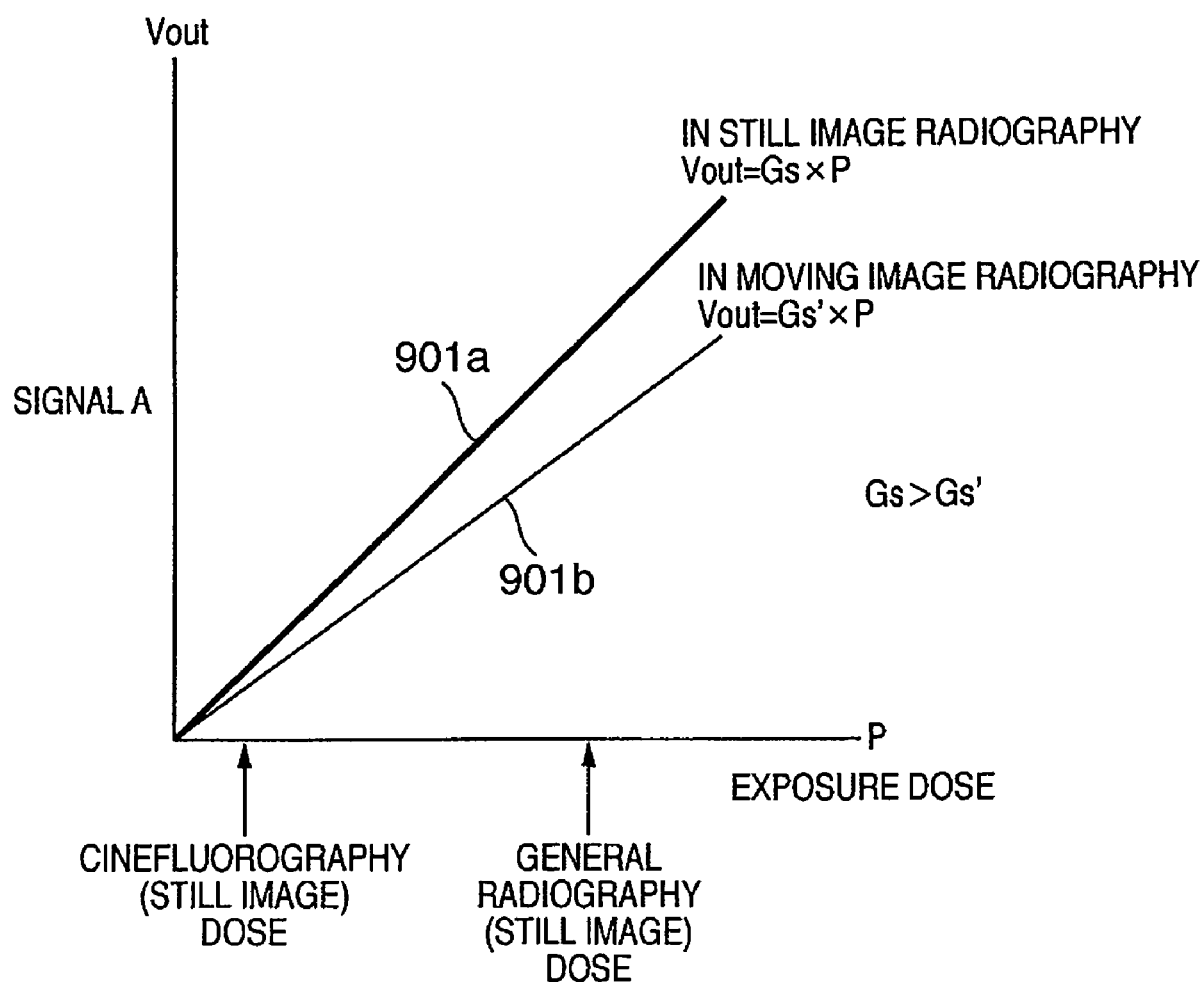

US 7,532,706 B2

IMAGING APPARATUS, IMAGING SYSTEM, IMAGING METHOD, AND COMPUTER PROGRAM

This is continuation of international application Serial No. PCT/JP 2005-014436, filed Aug. 5, 2005.

TECHNICAL FIELD

The present invention relates to an imaging apparatus, imaging system, imaging method, computer program, and is particularly suitable to correct the gain of a radiographed image.

BACKGROUND ART

The conventional technique will be described with reference to the accompanying drawings.

FIG. 7 is a block diagram showing the structure of a conventional radiographic imaging apparatus which performs image correction. FIG. 8 is a circuit diagram schematically showing the structure of a conventional imaging unit used in the radiographic imaging apparatus. Note that radiation includes X-, α-, β-, and γ-rays, and the like.

As shown in FIG. 8, the imaging unit 701 used in the conventional radiographic imaging apparatus has an area sensor 803 in which pixels are arrayed in a two-dimensional matrix to perform matrix driving. The pixels comprise conversion elements 801a to 801i which convert radiation into charges directly and switching elements 802a to 802i. As for the conversion elements 801a to 801i, for example, p-i-n photodiodes or MIS sensors can be used. The p-i-n photodiodes or MIS sensors are preferably formed from amorphous silicon. As for the switching elements 802a to 802i, for example, thin-film transistors (TFTs) can be used. A bias voltage Vs from a power supply 804 is applied to the common electrodes of the conversion elements 801a to 801i of the respective pixels. The gate electrodes of the switching elements 802a to 802i of the respective pixels are connected to common gate lines Vg1 to VgN. The common gate lines Vg1 to VgN are connected to a gate driving device 805 including shift registers (not shown) and the like. The source electrodes of the switching elements 802a to 802i are connected to common data lines Sig1 to SigM to output an image signal IS from a reading device 814 including a variable gain amplifier 811, analog multiplexer 812, A/D converter 813, and the like. Accordingly, the imaging unit 701 is formed from the area sensor 803, gate driving device 805, and reading device 814.

Image correction of the conventional radiographic imaging apparatus will be described with reference to FIG. 7. The image signal IS output from the imaging unit 701 is input to an offset correction unit 702. The offset correction unit 702 subtracts an offset correction signal OS based on offset data stored in an offset memory 703 in advance from the image signal IS to perform offset correction. The offset-corrected signal is input as a signal A to a gain correction unit 704. The gain correction unit 704 which corrects the gain characteristics of the respective pixels performs an arithmetic process such as division for the signal A and a gain correction signal GS based on gain correction data stored in a gain correction memory 705, to output the obtained result as a signal B to an output unit 706 such as a monitor (see patent references 1 and 2).

[Patent Reference 1] Japanese Patent Laid-Open No. 2003-244557

[Patent Reference 2] Japanese Patent Laid-Open No. 10-327317

While the conventional radiographic imaging apparatus has the offset correction unit 702 and gain correction unit 704, as described above, its gain correction signal corresponds to only a single mode.

As shown in FIGS. 9A and 9B, in the conventional radiographic imaging apparatus, the gain characteristics, i.e., input/output characteristics sometimes differ between moving image radiography in which radiography is performed continuously and still image radiography in which radiography is performed intermittently. In particular, according to experimental results, when the imaging unit 701 uses conversion elements formed from amorphous silicon, the difference in gain characteristics of the conversion elements between moving image radiography and still image radiography becomes obvious.

The difference in gain characteristics, i.e., input/output characteristics between moving image radiography and still image radiography will be described in detail. Note that in the specification, "gain characteristics" is used in a broad sense and means input/output characteristics, i.e., sensitivity characteristics.

A charge amount Q generated in the conversion element and input to each column of the reading device after radiation is transmitted through an object can generally be expressed for an incident photon (radiographic quantum) count P by $$Q(\text{col,row}) = Gs(\text{col,row}) \times p^{\gamma(\text{col,row})}$$

where $Gs(\text{col,row})$ is a gain or quantum efficiency specific to a pixel at each (col (column),row), and $\gamma$ (col,row) is an index (generally called gamma) specific to a pixel at each (col (column),row).

An analog output Vout which is output from an analog multiplexer of the reading device and corresponds to respective pixels can be expressed by $$V\text{out}(\text{col,row}) = Q(\text{col,row}) \times Ga(\text{col})/Cf(\text{col})$$

where $Ga(\text{col})$ is the gain of an amplifier (not shown in FIG. 8) provided to each column of the reading device, and $Cf(\text{col})$ is the storage capacitance of the amplifier provided to each column of the reading device.

Accordingly, an analog output finally output from the analog multiplexer of the reading device can be expressed by the following approximate expression.

$$V\text{out}(\text{col,row}) = Gs(\text{col,row}) \times p^{\gamma(\text{col,row})} \times Ga(\text{col})/Cf(\text{col})$$

The present inventor has newly found that both $Gs(\text{col,row})$ and $\gamma(\text{col,row})$ depend on the following factors (1) to (5).

(1) the opening ratio, film thickness, film quality, and capacitance of the conversion element (2) an electrical field applied to the conversion element (3) if a phosphor is present, its film thickness and film quality (when the conversion element is a photoelectric conversion element)

(4) an environmental temperature (5) the history of radiation (or light) irradiation or history of electrical field application When the reading device is formed from an integrated circuit (IC) or the like, it should be noted that $Ga(\text{col})$, $Cf(\text{col})$, and the like, are nonuniform amounts which vary in accordance with the manufacturing process.

In a radiographic imaging apparatus, generally, not only a frame rate but also a dose to be applied to an object to obtain one image differs greatly between general radiography (still image) and fluorography (moving image). A charge amount generated in the conversion element differs greatly as well. Particularly, in an X-ray imaging apparatus using X-rays as radiation, in order to decrease a radiation dose of an object, a dose in fluorography (moving image) is sometimes decreased by at least one order of magnitude compared to that in general radiography (still image).

That is, when the gain Ga(col) or Cf(col) of the reading device is changed between general radiography (still image) and fluorography (moving image) in order to adjust an output range, variations in Ga or Cf in the reading device manufacturing process become a nonnegligible amount. Consequently, a correction error may occur in a correction method of the conventional radiographic imaging apparatus.

Furthermore, because the characteristics of the conversion element change depending on the above-described factors (1) to (5), for example, when an electrical field applied to the conversion element is changed in general radiography (still image) and fluorography (moving image), gain characteristics can change. Consequently, a correction error may occur in the correction method of the conventional radiographic imaging apparatus.

In addition, even when the history of radiation irradiation, history of electrical field application, environmental temperature, or the like differs between general radiography (still image) and fluorography (moving image), a correction error may occur in a correction method of the conventional radiographic imaging apparatus.

An example in which gain characteristics between general radiography (still image) and fluorography (moving image) change according to the history of electrical field application and that of radiation irradiation will be described below with reference to FIGS. 9A and 9B.

The X-ray dose to be applied to the conversion element and the frame rate differ between moving image radiography and still image radiography. The response speed of light when charges are trapped by the amorphous silicon, which is used in a conversion layer (i.e., a layer for converting radiation into charges directly) of the conversion element, can change between moving image radiography and still image radiography. This may cause a difference in gain characteristics of the conversion element as shown in FIGS. 9A and 9B.

In the case of still image radiography, sometimes the power supply of the imaging unit 701 is turned off for each radiographic operation. In this case, a bias applied to the conversion element 801 is also turned off. In the case of moving image radiography, radiographic operation is performed continuously while the power supply of the imaging unit 701 is kept on. In this case, a bias is continuously applied to the conversion element 801 during the radiographic operation. When the conversion element 801 of the imaging unit 701 is formed from amorphous silicon, such a difference in history of power supply application, i.e., a difference in history of bias application to the conversion element 801 may appear as a difference in gain characteristics of the conversion element.

The difference in gain characteristics as described above appears in several manners. For example, as shown in FIG. 9A, sometimes the sensitivity differs between still image radiography and moving image radiography. Also, as shown in FIG. 9B, sometimes gamma (γ) differs between still image radiography and moving image radiography. Although not shown in FIGS. 9A and 9B, sometimes gain characteristics 901*a* and 901*b* shown in FIG. 9A overlap gain characteristics 902*a* and 902*b* shown in FIG. 9B, and accordingly both the sensitivity and gamma differ between still image radiography and moving image radiography. These phenomena indicate that when the signal A obtained in moving image radiography is corrected by a gain correction signal suited to still image radiography, sometimes a correction error may occur.

Patent references 1 and 2 describe the functions of offset correction and gain correction. However, these references do not describe at all the correction error caused by a difference in gain characteristics according to the radiographic mode.

A correction error occurs, when the gain characteristics according to a frame rate, dose to radiograph one image, and usage method differ between moving image radiography and still image radiography, as the conventional X-ray imaging apparatus has only a gain correction signal which corresponds to a single mode, as described above. More specifically, when both moving image radiography and still image radiography are performed by the conventional X-ray imaging apparatus, gain correction is not performed appropriately, and sometimes the image quality is degraded.

DISCLOSURE OF INVENTION

The present invention has been made in view of the problems above, and has as its object to enable image correction appropriately regardless of the radiographic mode.

According to the present invention, there is provided an imaging apparatus comprising a gain correction unit which corrects, in order to correct at least gain characteristics of a plurality of conversion elements, a gain of an image signal from an imaging unit having the plurality of conversion elements using a correction signal stored on a storage medium, characterized in that the gain correction unit is arranged to correct the gain of the image signal using different correction signals in accordance with a plurality of radiographic modes.

According to the present invention, there is provided an imaging apparatus comprising a gain correction unit which corrects, in order to correct at least gain characteristics of a plurality of conversion elements, a gain of an image signal from an imaging unit having the plurality of conversion elements using a correction signal stored on a storage medium, characterized in that the gain correction unit is arranged to correct the gain of the image signal using different correction signals in accordance with a radiation dose to be applied to the imaging unit in order to obtain the image signal for one image.

According to the present invention, there is provided an imaging system comprising an imaging apparatus which has an imaging unit including a plurality of conversion elements, and a gain correction unit which corrects, in order to correct at least gain characteristics of the conversion elements, a gain of an image signal from the imaging apparatus using a correction signal stored on a storage medium, characterized in that the gain correction unit is arranged to correct the gain of the image signal using different correction signals in accordance with a plurality of radiographic modes.

According to the present invention, there is provided an imaging system comprising an imaging apparatus which has an imaging unit including a plurality of conversion elements, and a gain correction unit which corrects, in order to correct at least gain characteristics of the conversion elements, a gain of an image signal from the imaging apparatus using a correction signal stored on a storage medium, characterized in that the gain correction unit is arranged to correct the gain of the image signal using different correction signals in accordance with a radiation dose to be applied to the imaging unit in order to obtain the image signal for one image.

According to the present invention, there is provided an imaging method characterized by comprising an imaging step of capturing an image of an object by an imaging unit having a plurality of conversion elements, and a gain correction step of correcting, in order to correct at least gain characteristics of the conversion elements, a gain of an image signal of the object which is captured in the imaging step using a correction signal stored on a storage medium, wherein in the gain correction step, the gain of the image signal is corrected using different correction signals in accordance with a plurality of radiographic modes.

According to the present invention, there is provided a computer program which causes a computer to correct at least gain characteristics of a plurality of conversion elements for an image signal of an object, which is captured by an imaging unit having the plurality of conversion elements, using different correction signals in accordance with a plurality of radiographic modes.

According to the present invention, there is provided a computer program which causes a computer to correct at least gain characteristics of a plurality of conversion elements for an image signal of an object, which is captured by an imaging unit having the plurality of conversion elements, using different correction signals in accordance with a radiation dose to be applied to the imaging unit in order to obtain the image signal for one image.

According to the present invention, a gain of an image signal of an object which is captured by an imaging unit is corrected using different correction signals in accordance with a plurality of radiographic modes. Even when image capturing is performed using an imaging unit having different gain characteristics according to the radiographic mode, a good image with decreased correction errors can be acquired regardless of the radiographic mode.

According to the present invention, a gain of an image signal of an object which is captured by an imaging unit is corrected using different correction signals in accordance with a radiation dose to be applied to the imaging unit in order to obtain the image signal for one image. Even when image capturing is performed using an imaging unit having different gain characteristics according to the radiation dose, a good image with decreased correction errors can be acquired regardless of the radiation dose.

Other features and advantages of the present invention will be apparent from the following description taken in conjunction with the accompanying drawings, in which like reference characters designate the same or similar parts throughout the figures thereof.

BRIEF DESCRIPTION OF DRAWINGS

The accompanying drawings, which are incorporated in and constitute a part of the specification, illustrate embodiments of the invention and, together with the description, serve to explain the principles of the invention.

FIG. 9A is a graph showing the gain characteristics of the conventional X-ray imaging apparatus;

BEST MODE FOR CARRYING OUT THE INVENTION

The preferred embodiments of the present invention will be described in detail with reference to the accompanying drawings.

First Embodiment

The first preferred embodiment of the present invention will be described.

Figure 1:
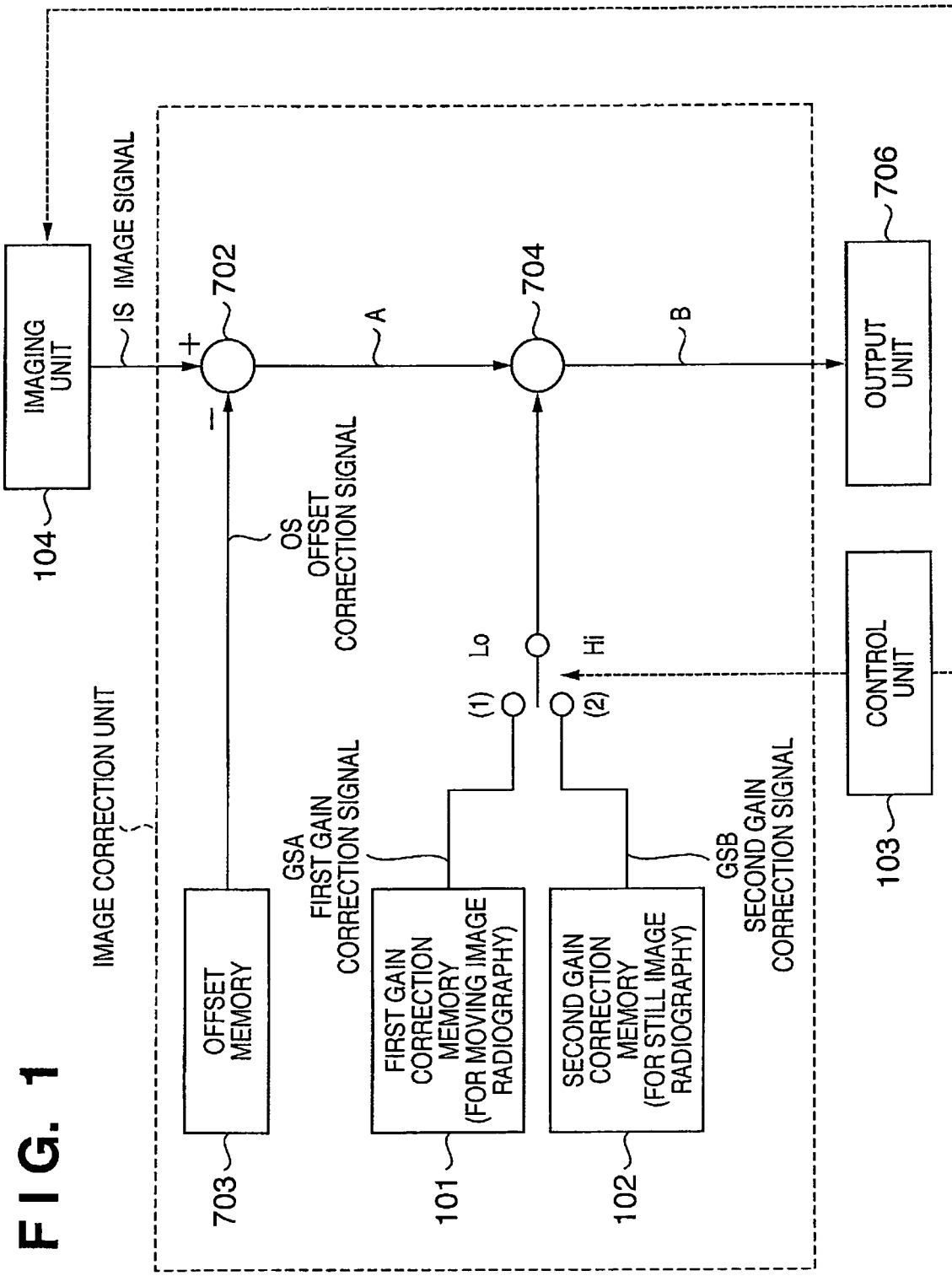
FIG. 1 is a block diagram of a first preferred embodiment of the present invention and shows an example of the structure of an X-ray imaging apparatus which performs image correction.
Figure 2:
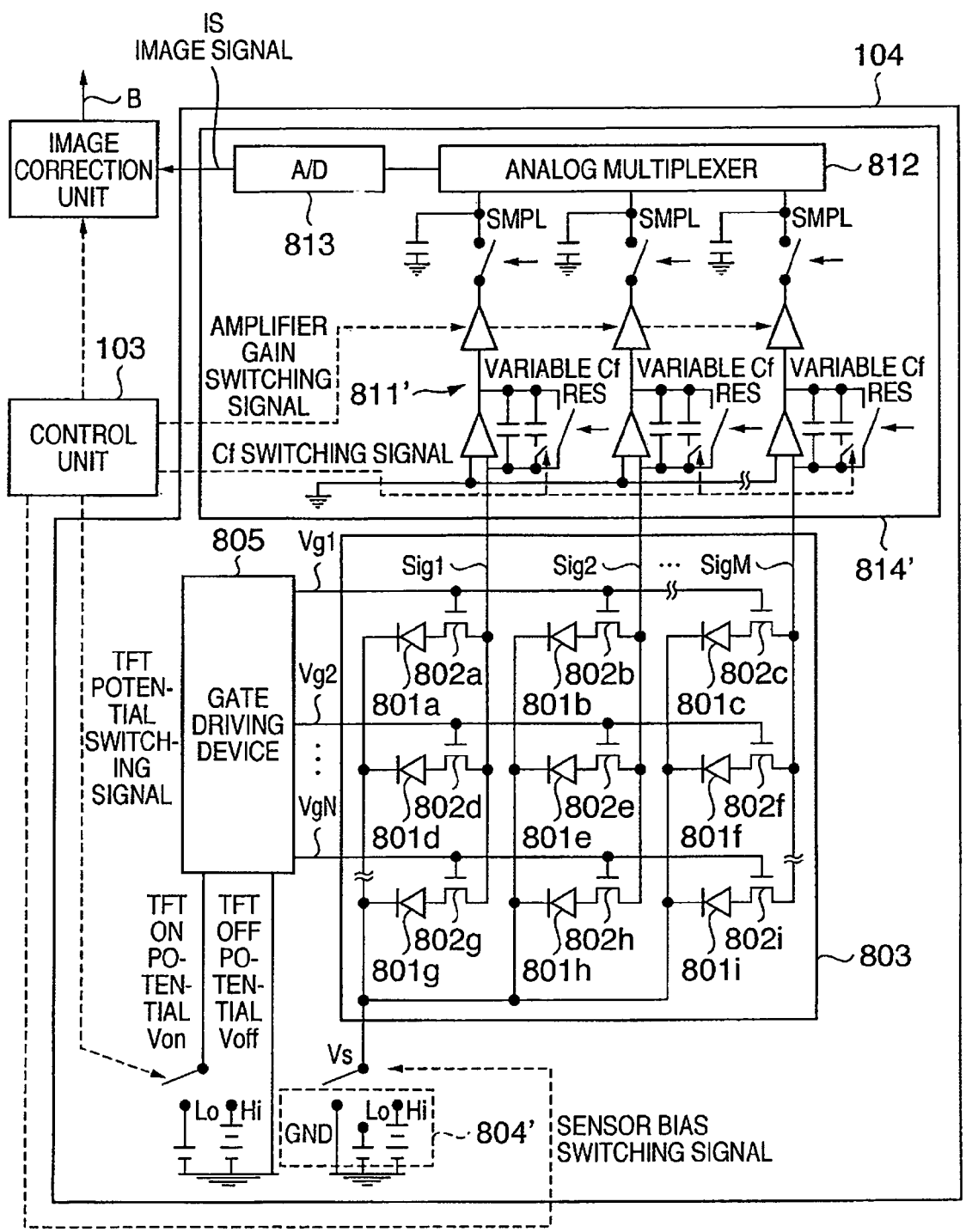
FIG. 2 is a circuit diagram of the first preferred embodiment of the present invention and schematically shows an example of the structure of an imaging unit which is included in the X-ray imaging apparatus.
Figure 3:
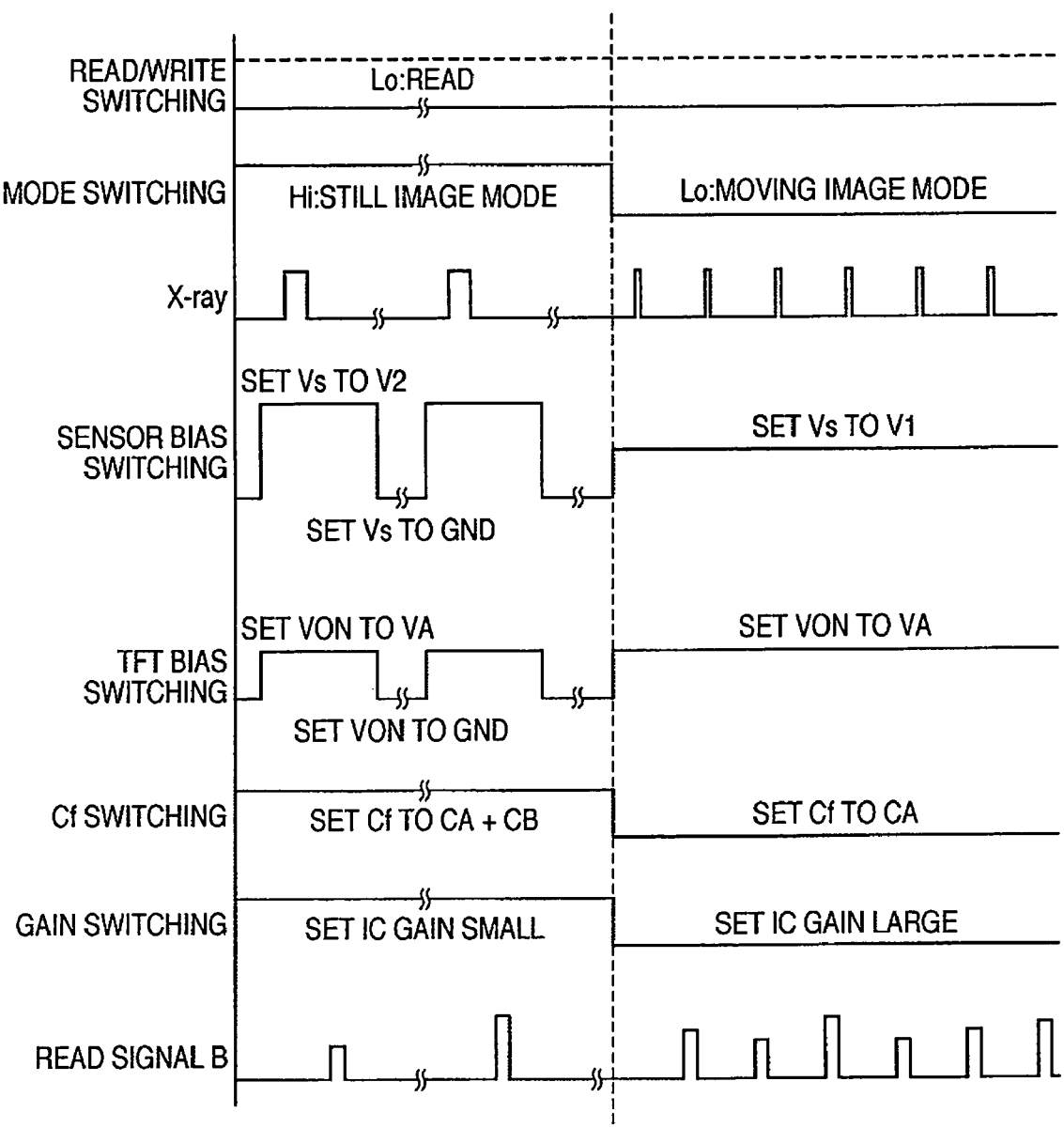
FIG. 3 is a timing chart of the first preferred embodiment of the present invention and explains an example of the operation of the X-ray imaging apparatus when performing image correction.
Figure 4:
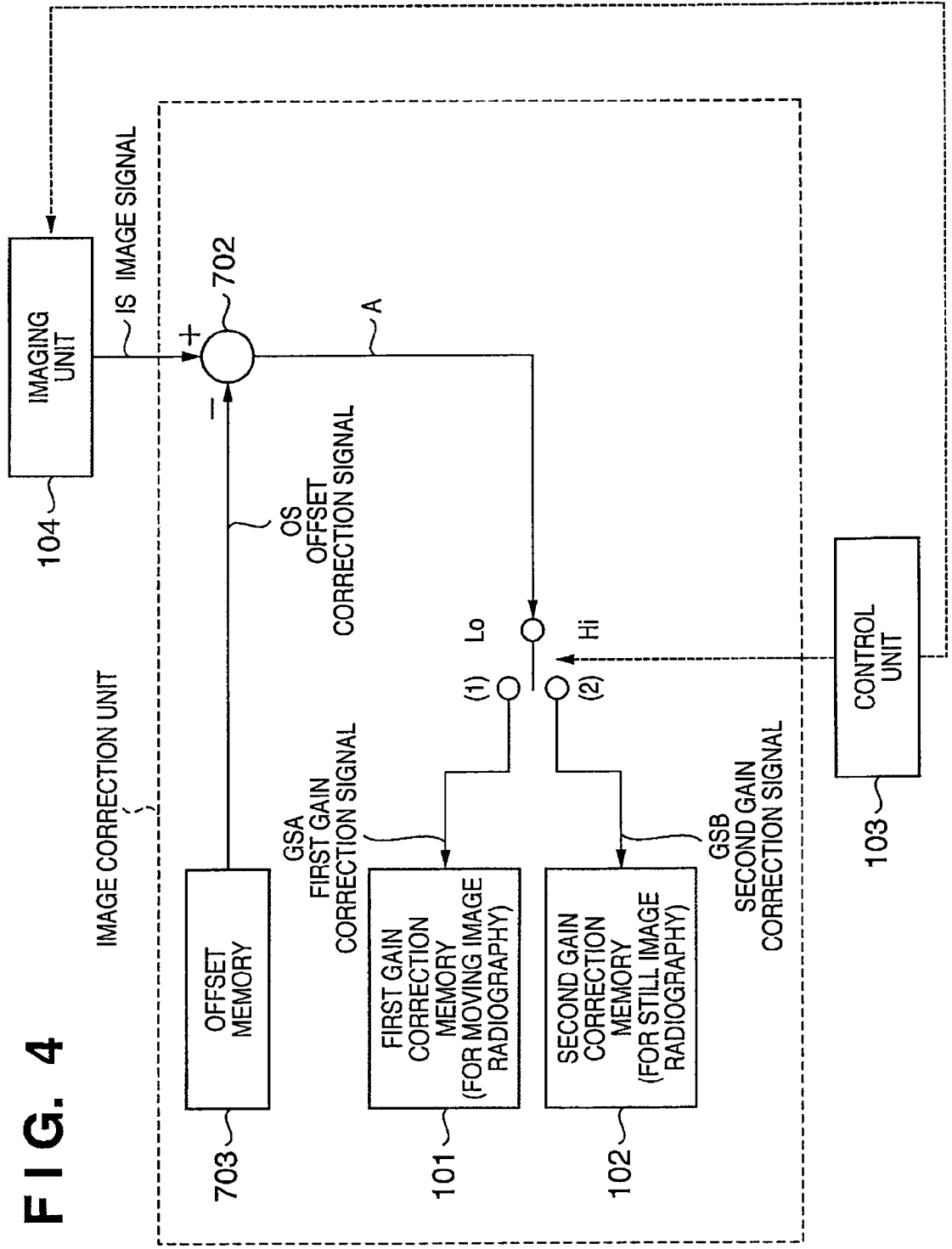
FIG. 4 is a block diagram of the first preferred embodiment of the present invention and shows an example of the structure of the X-ray imaging apparatus which sets and updates a gain correction signal to perform image correction.
Figure 5:
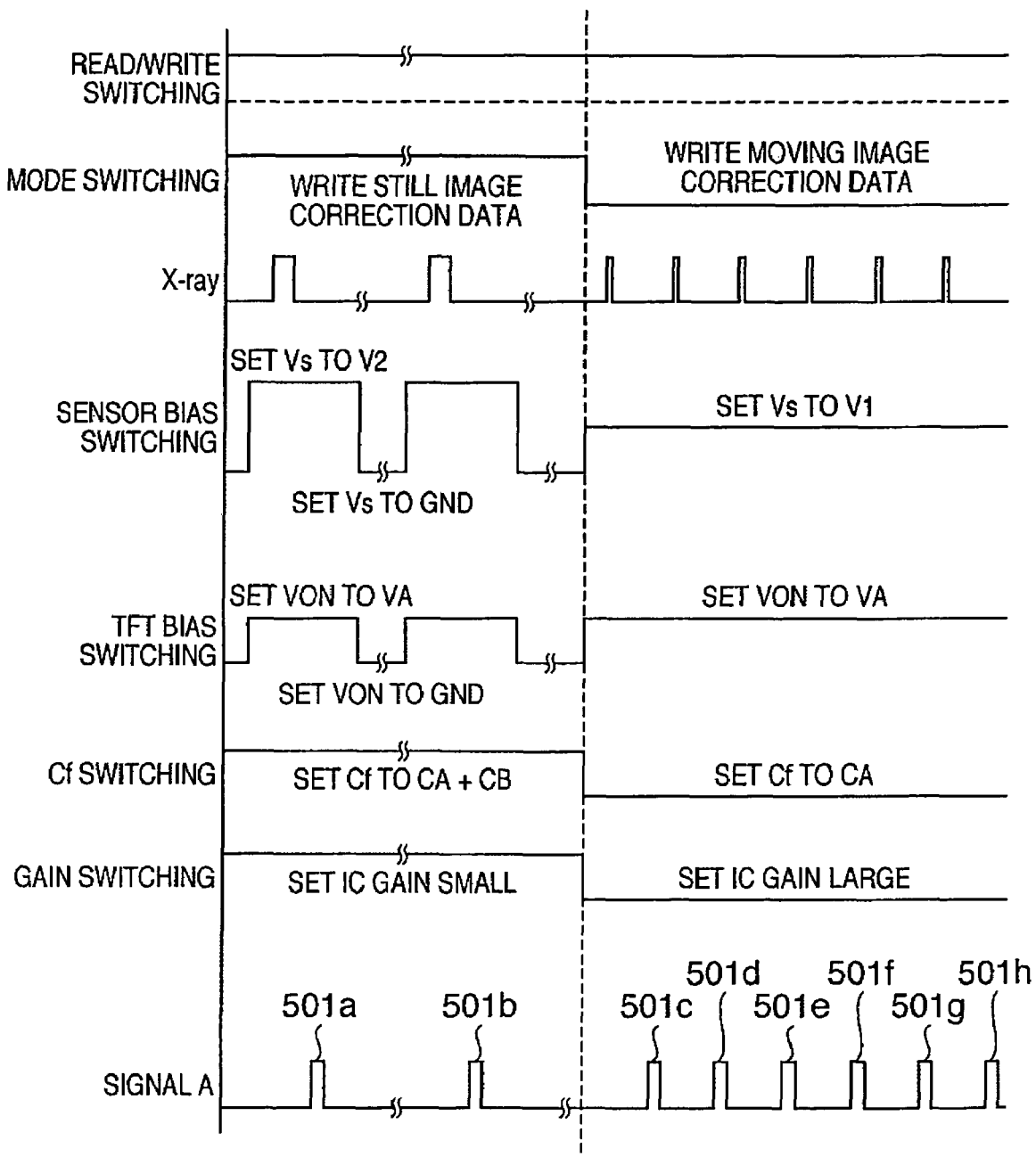
FIG. 5 is a timing chart of the first preferred embodiment of the present invention and explains an example of the operation of the X-ray imaging apparatus when setting and updating the gain correction signal to perform image correction.
Figure 6:
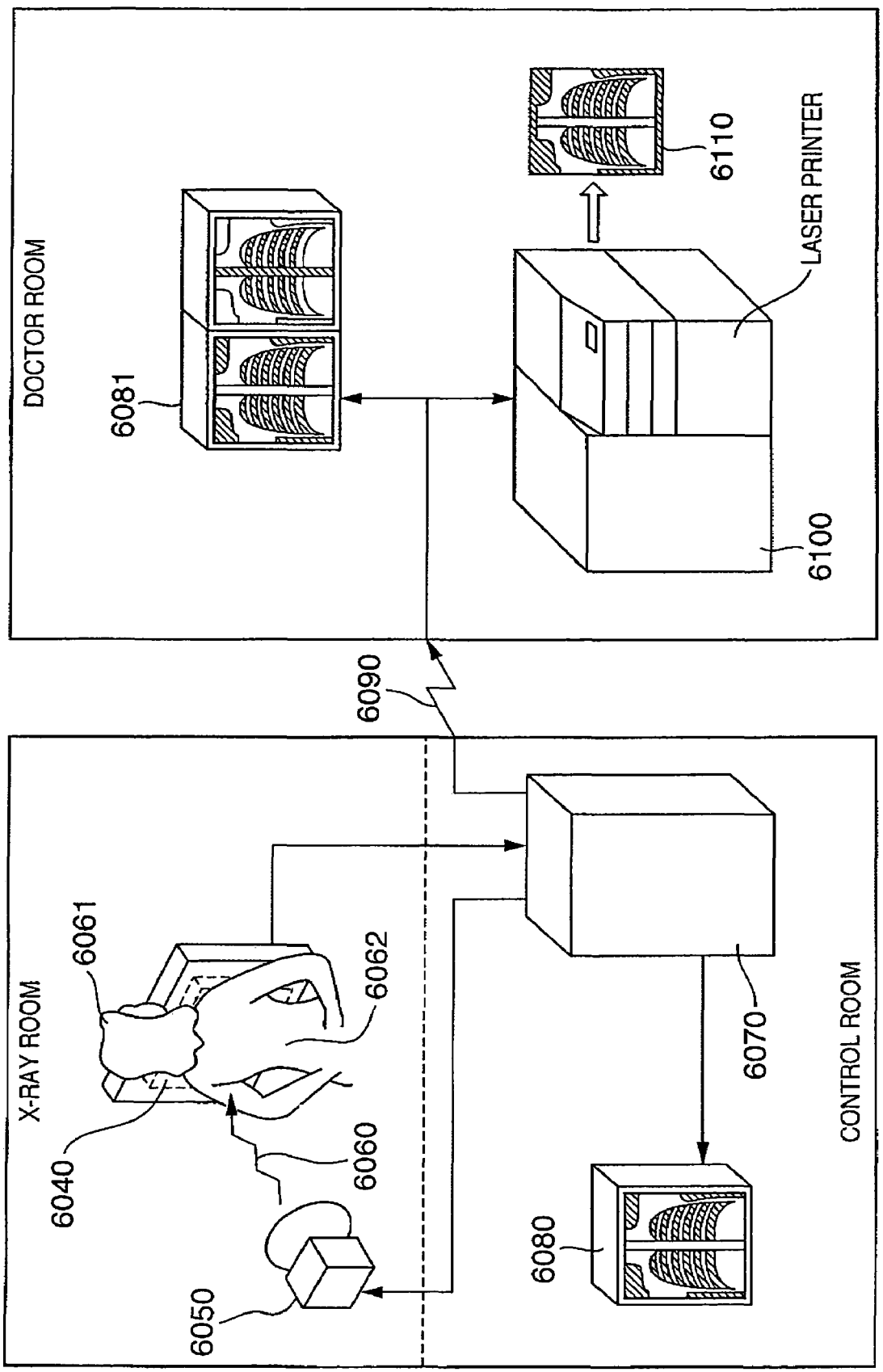
FIG. 6 is a view of the second preferred embodiment of the present invention and shows an example of the structure of a radiographic system.
Figure 9B:
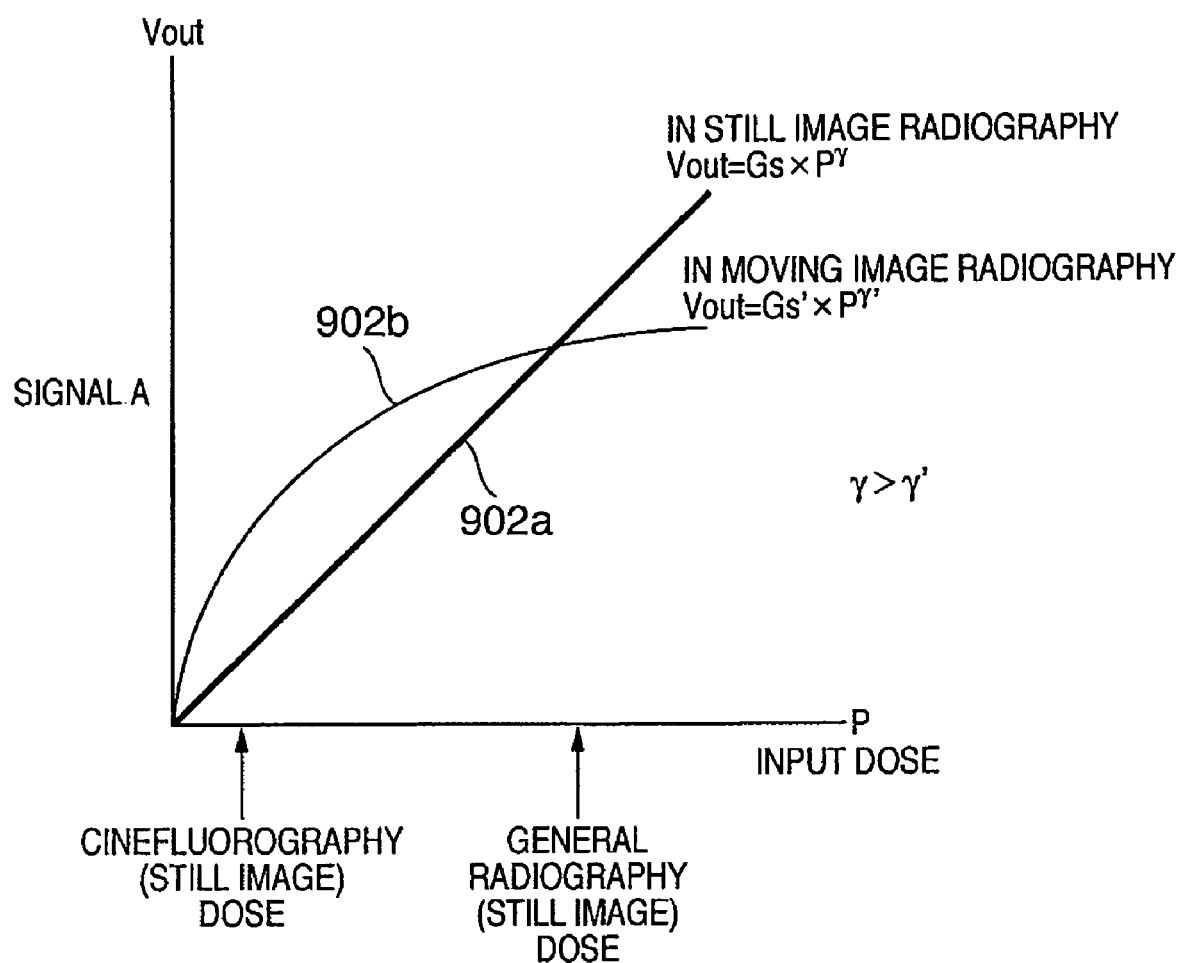
FIG. 9B is a graph showing the gain characteristics of the conventional X-ray imaging apparatus.
Figure 10A:
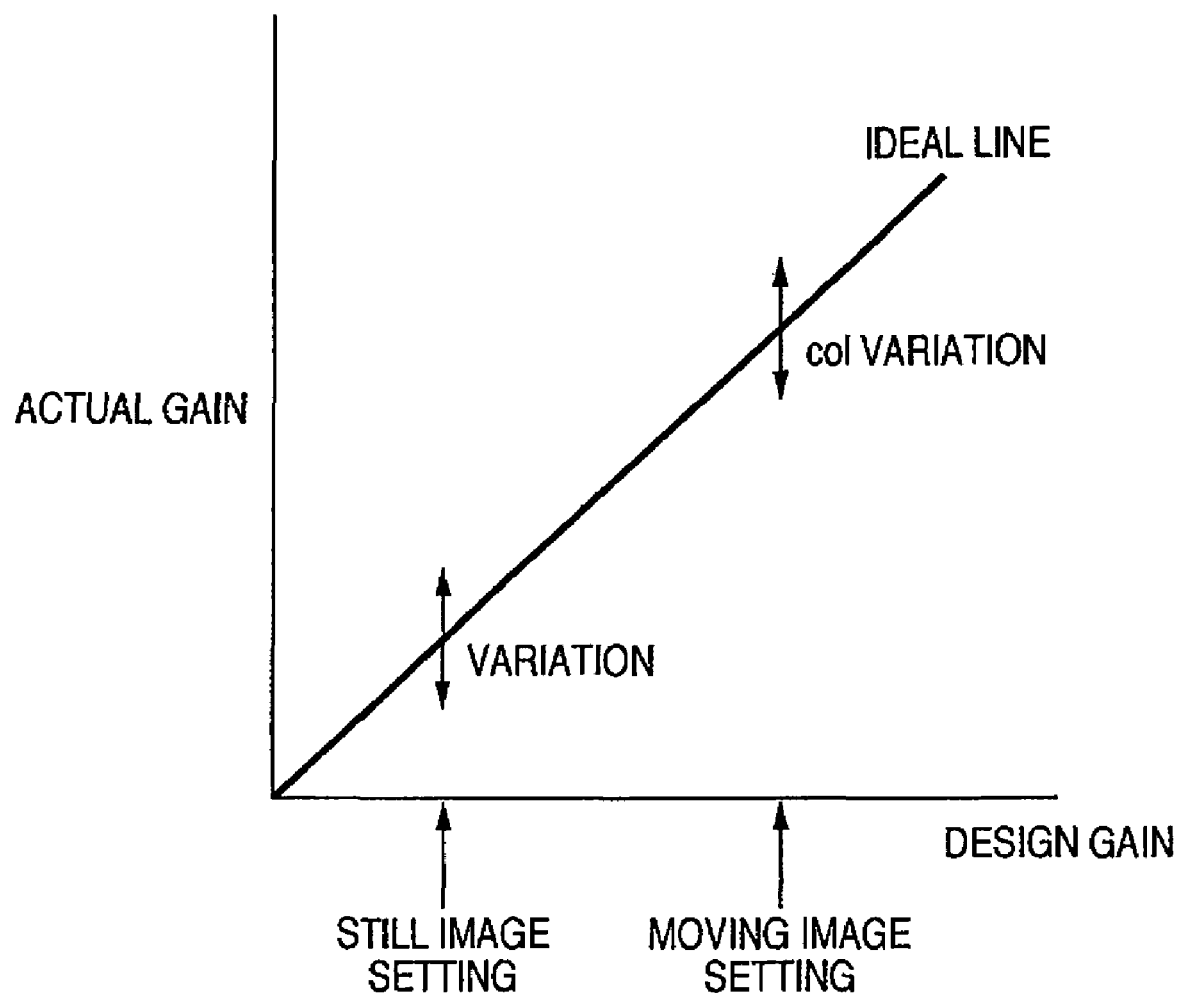
FIG. 10A is a graph for explaining the characteristics of a conversion element of a reading device used in the first embodiment.
Figure 10B:
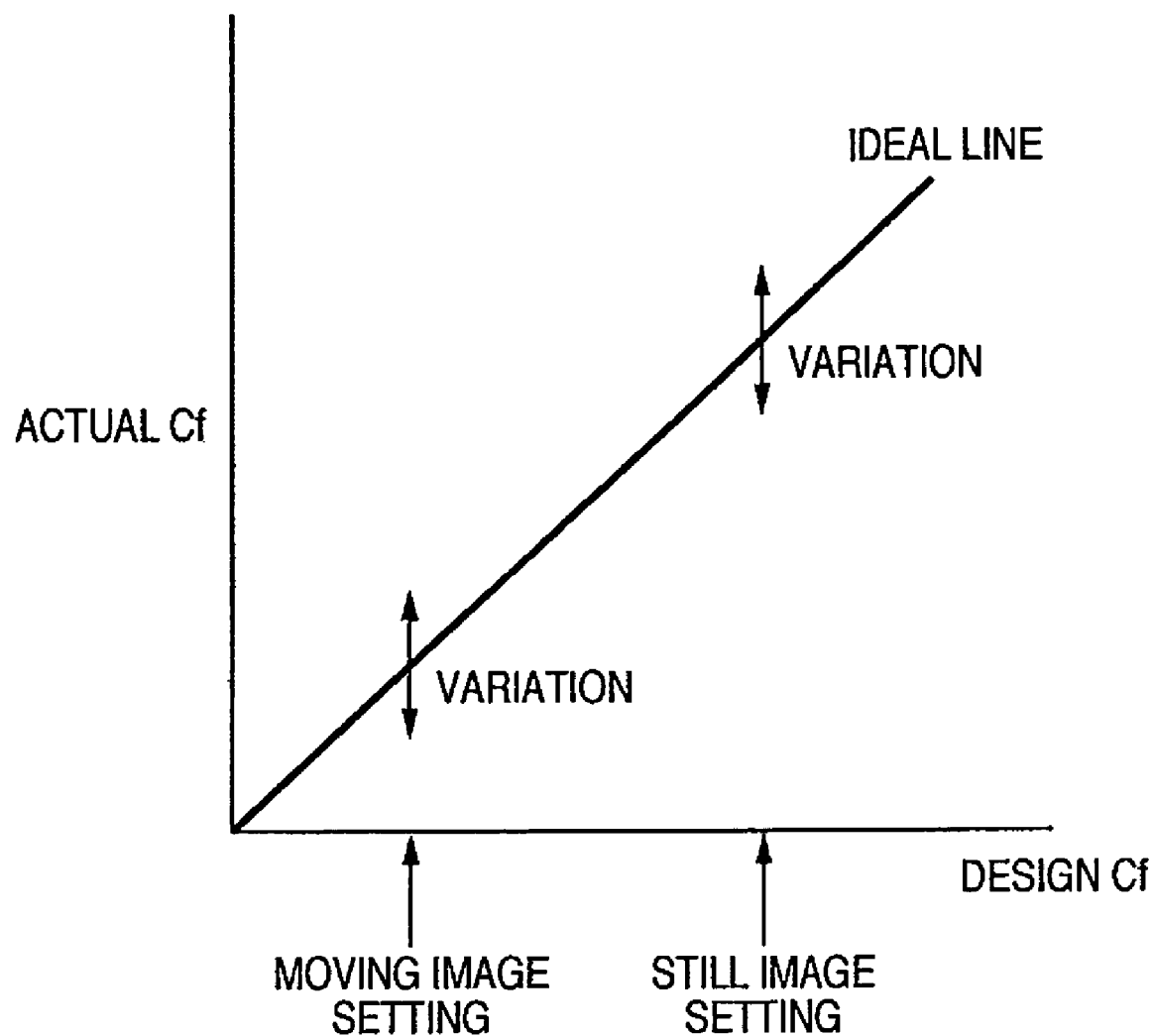
FIG. 10B is a graph for explaining the characteristics of the conversion element of the reading device used in the first embodiment.
Figure 10C:
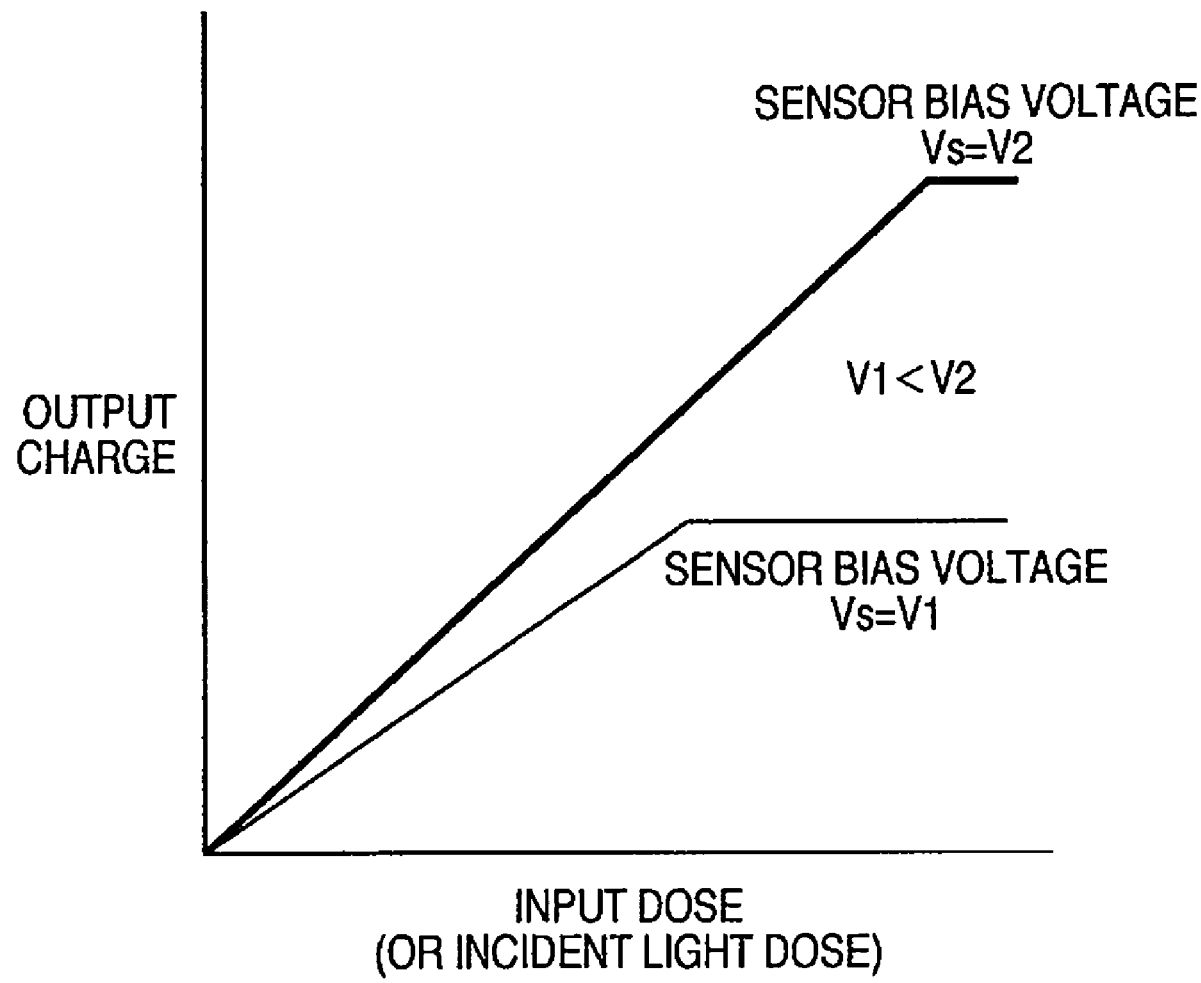
FIG. 10C is a graph for explaining the characteristics of the conversion element of the reading device used in the first embodiment.

FIGS. 1 and 4 are block diagrams of the first preferred embodiment of the present invention and explain the first and second examples of the structure of an X-ray imaging apparatus which performs image correction. FIG. 2 is a circuit diagram of the first preferred embodiment of the present invention and schematically shows an example of the structure of an imaging unit which is included in the X-ray imaging apparatus. FIGS. 3 and 5 are timing charts of the first preferred embodiment of the present invention and explain the first and second examples of the operation of the X-ray imaging apparatus. FIG. 6 is a view of a preferred embodiment of the present invention and shows an example of the structure of an X-ray radiographic system which uses an X-ray imaging apparatus. In FIGS. 1 to 6, the similar constituent elements as in FIGS. 7 to 9B described above are denoted by the same reference numerals, and a detailed description thereof will be omitted. FIGS. 10A to 10C are graphs for explaining the characteristics of a conversion element according to a gain, Cf variation and bias application of a reading device which is used in the first embodiment.

Figure 7:
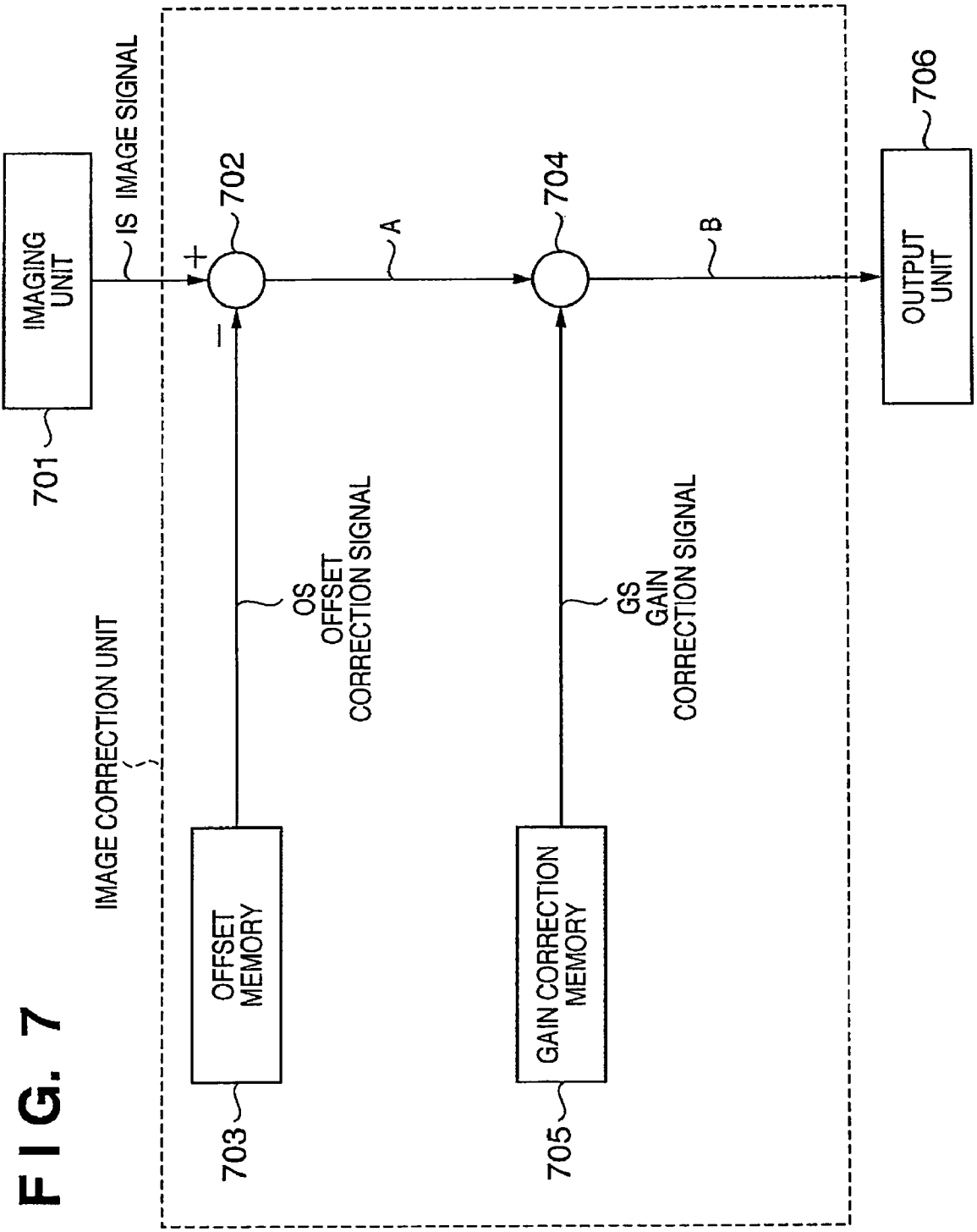
FIG. 7 is a block diagram showing the structure of a conventional X-ray imaging apparatus which performs image correction.
Figure 8:
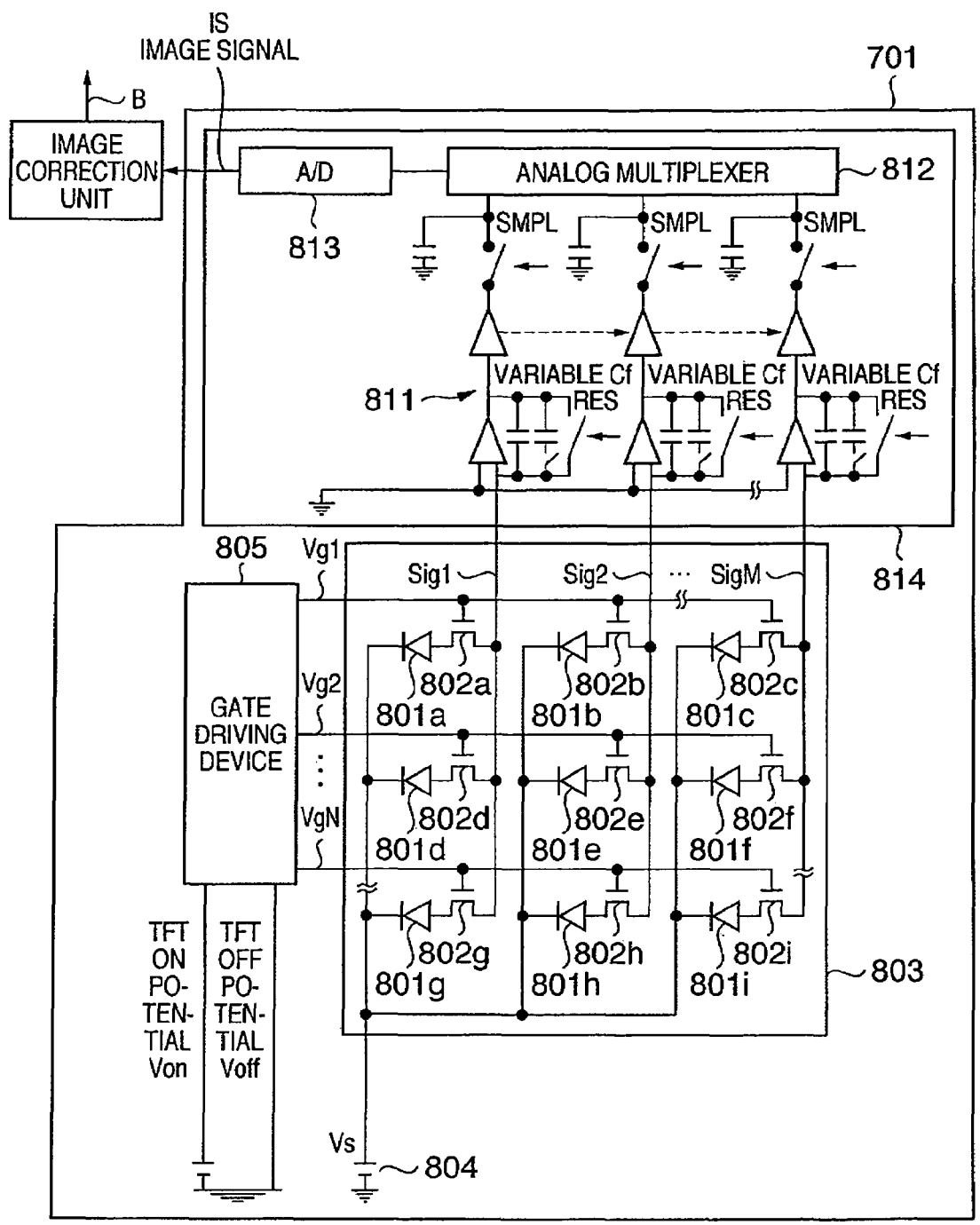
FIG. 8 is a circuit diagram schematically showing the structure of a conventional imaging unit which is used in the X-ray imaging apparatus.

As shown in FIG. 1, when compared to the conventional X-ray imaging apparatus shown in FIG. 7, the X-ray imaging apparatus according to this embodiment is different in the following respects.

(1) The X-ray imaging apparatus according to this embodiment has a first gain correction memory 101 for moving image radiography and a second gain correction memory 102 for still image radiography.

(2) The X-ray imaging apparatus according to this embodiment has a control unit 103 and can switch a gain correction signal GSA based on gain correction data for moving image radiography and a gain correction signal GSB based on gain correction data for still image radiography, to be input to a gain correction unit 704 in accordance with the radiographic mode (moving image radiographic mode/still image radiographic mode).

More specifically, the control unit 103 causes the first gain correction signal GSA based on the gain correction data for moving image radiography to be input to the gain correction unit 704 in the moving image radiographic mode, and the second gain correction signal GSB based on the gain correction data for still image radiography to be input to the gain correction unit 704 in the still image radiographic mode. Furthermore, the control unit 103 can control the operation of the imaging unit shown in FIG. 2 in accordance with the radiographic mode. Although not shown, the control unit 103 is preferably formed to be capable of controlling in accordance with the radiographic mode the operation of an X-ray generating device which outputs radiation toward an object.

In this manner, in the respective radiographic modes (moving image radiographic mode/still image radiographic mode) set in the X-ray imaging apparatus, a correction process is performed using the different gain correction signals GSA and GSB. Even when the X-ray imaging apparatus is formed using an imaging unit having different gain characteristics in the still image radiographic mode and moving image radiographic mode, as shown in FIGS. 9A and 9B, an image with decreased correction errors can be acquired. In other words, a radiographed image can be appropriately corrected in either of the still image radiographic mode and moving image radiographic mode.

For example, the X-ray imaging apparatus according to this embodiment is formed as shown in FIG. 2. When compared to the conventional X-ray imaging apparatus shown in FIG. 8, the X-ray imaging apparatus according to this embodiment is different in that the control unit 103 can control the ON/OFF operation of a sensor bias voltage Vs and an ON potential Von of switching elements (e.g., TFTs) 802a to 802i. In addition to the ON/OFF operation of the sensor bias voltage Vs (804'), the X-ray imaging apparatus is different from the conventional one in that the sensor bias potential can be switched between V1 (Lo) and V2 (Hi) corresponding to the moving image radiography and still image radiography. Also, the X-ray imaging apparatus is different from the conventional one in that a storage capacitance Cf of a preamplifier and a gain of a variable gain amplifier 811' which are connected to respective signal lines in the reading device 814' can be switched between the moving image radiography and still image radiography. The operation of performing image correction (image reading) by the X-ray imaging apparatus according to this embodiment will be described in more detail with reference to FIGS. 1 to 3.

First, the read operation in the still image radiographic mode will be described. As shown in FIG. 3, for example, when a read/write switching signal generated in e.g., a workstation (not shown) in response to the operation of the user of the X-ray imaging apparatus is Lo, it indicates read operation. When a mode switching signal is Hi, it indicates the still image radiographic mode (i.e., general radiography). In this case, the control unit 103 causes the second gain correction signal GSB to be input to the gain correction unit 704 (see FIG. 1).

The control unit 103 also causes a bias switching signal to be input to control the sensor bias voltage Vs and the ON potential Von of the switching element (e.g., a TFT) 802 (see FIG. 2). The ON/OFF timing of the bias switching signal is as shown in FIG. 3. More specifically, in the still image radiographic mode, a sensor bias voltage Vs is set to V2 and every time one frame is to be radiographed, the sensor bias voltage Vs and the ON potential Von of the switching element (e.g., a TFT) 802 are turned off (set to the GND potential). In other words, every time one frame is to be radiographed, the respective types of potentials to be applied to the area sensor become the GND potential. This embodiment is set such that an OFF potential Voff of the switching element (e.g., a TFT) is fixed at GND. Alternatively, the OFF potential Voff of the switching element (e.g., a TFT) can be switched to another potential (e.g., a negative potential). In this case, every time one frame is to be radiographed, the OFF potential Voff of the switching element (e.g., a TFT) is set to the GND potential, in the same manner as the sensor bias voltage Vs and ON potential Von of the switching element (e.g., a TFT).

In this manner, temporarily setting the potential applied to the area sensor to the GND potential every time one frame is to be radiographed has an effect to initialize the characteristics of the area sensor. More specifically, an afterimage may be decreased.

In the still image radiographic mode, the control unit sets the storage capacitance of the preamplifier connected to the respective signal lines in the reading device to CA+CB, and the gain of the variable gain amplifier to "low" compared to that in the moving image radiographic mode. In this manner, setting the storage capacitance "large" and the variable gain "low" compared to those in the moving image radiographic mode can allow the read operation to be performed without being saturated even for a relatively large dose of several mR (milliroentgen).

After the X-rays are radiated, a signal B corrected by the second gain correction signal GSB for still image radiography is output to an output unit 706.

The read operation in the moving image radiographic mode will be described. As shown in FIG. 3, when the mode switching signal generated in response to the operation of the user of the X-ray imaging apparatus is Lo, it indicates the moving image radiographic mode. In this case, the control unit 103 causes the first gain correction signal GSA to be input to the gain correction unit 704 (see FIG. 1).

The control unit 103 fixes the sensor bias voltage Vs at V1 and keeps ON the ON potential Von of the switching element (e.g., a TFT) 802. The timing to switch ON the bias switching signal is as shown in FIG. 3.

In the moving image radiographic mode, as shown in FIG. 3, the storage capacitance of the preamplifier of the reading device is set to CA and the gain of the variable amplifier is set to "high". This allows to obtain a good image even for a dose which is smaller by at least one order of magnitude than that in still image radiography. It should be noted that in the moving image radiographic mode, X-ray pulse period is greatly shorter than that in the still image radiographic mode.

When the X-rays are radiated, the signal B corrected by the first gain correction signal GSA for moving image radiography is output to the output unit 706 at a constant cycle.

The correction process in the gain correction unit described above is preferably an arithmetic process using e.g., an approximate expression. When a higher-speed processing is needed, a large number of memories are required, and the correction process may be performed using e.g., a look-up table (LUT).

How to set and update the first gain correction signal GSA for moving image radiography and the second gain correction signal GSB for still image radiography will be described with reference to FIGS. 4, 5, and 10A to 10C.

Differences between the still image radiographic mode and moving image radiographic mode according to this embodiment will be described with reference to FIGS. 10A to 10C. Because a dose is greatly different in the still image radiographic mode and moving image radiographic mode as described above, the storage capacitance Cf and the gain of the reading device can be changed by a signal from the control unit in this embodiment (as shown in FIG. 2). On the other hand, as shown in FIGS. 10A and 10B, the Cf and gain of the reading device have variations due to a manufacturing process. Accordingly, to obtain correct gain correction data, it is desirable to set a Cf and gain corresponding to respective radiographic modes and acquire gain correction data.

Also, as shown in FIG. 10C, the sensitivity characteristics of the conversion element may depend on the sensor bias voltage Vs. When the conversion element is formed from a p-i-n photodiode or MIS sensor using amorphous silicon, the following relationship is given. That is, when the sensor bias voltage is high, the sensitivity and saturation are also high, and vice versa, as shown in FIG. 10C. Note that when the sensor bias voltage is high, characteristic degradation may be induced. For this reason, a high sensor bias voltage is not always regarded as appropriate and different sensor bias voltages are properly used in accordance with the radiographic modes as in this embodiment.

First, the write operation of the gain correction data in the still image radiographic mode will be described.

As shown in FIG. 5, the state wherein the read/write switching signal is Hi indicates correction data write operation. When the mode switching signal is Hi, the correction data is written in the second gain correction memory 102 for still image radiography. More specifically, with no object, an imaging unit 104 is irradiated with the X-rays, and a signal A corresponding to pulse signals 501a and 501b shown in FIG. 5 is obtained. In this case, at least one of the sensor bias voltage, bias voltage of the switching element (e.g., a TFT), and Cf and gain of the reading device is preferably so controlled by the control unit as to be equal to those in reading operation. More preferably, the control unit controls the X-ray generating device (not shown) to output an X-ray dose which is equal to that generally output in still image radiography. In order to obtain an image needed for diagnosis, the present inventor takes into account a maximum dose of 1 mR to several ten mR per frame to be applied to the surface of the area sensor in the still image radiographic mode according to this embodiment in consideration of an effect of X-ray quantum noise. For this reason, the Cf and gain in the still image radiographic mode are preferably set not to be saturated with the above dose. A dose to be applied in acquiring the correction data is preferably at least 0.1 mR to 1 mR per frame from the viewpoint of correction accuracy.

The signal A is directly written in the second gain correction memory 102. Averaging the pulse signals 501a and 501b by an arithmetic operation unit (not shown) or the like is preferable in improving the correction accuracy.

When the mode switching signal is Lo, the correction data is written in the first gain correction memory 101 for moving image radiography. More specifically, with no object, the imaging unit 104 is irradiated with X-rays periodically or continuously to obtain the signal A corresponding to pulse signals 501c to 501h shown in FIG. 5. The signal A is directly written in the first gain correction memory 101. In improving the correction accuracy, it is preferable to average the pulse signals 501c to 501h by the arithmetic operation unit (not shown) or the like. It is more preferable to average the pulse signals 501d to 501h or the like excluding the pulse signal 501c and write the obtained average in the first gain correction memory 101 in order to decrease the influence of the history of X-ray irradiation. Furthermore, as in the case of writing correction data for a moving image, the control unit preferably sets at least one of the sensor bias, bias of the switching element (e.g., a TFT), and Cf and gain of the reading device to the same condition as in moving image radiography. The control unit more preferably controls the X-ray generating device (not shown) to apply a dose as in the moving image radiographic mode. In the moving image radiographic mode according to this embodiment, a maximum dose of 10 uR to several hundred uR per frame is taken into account for the surface of the area sensor. For this reason, the Cf and gain in the moving image radiographic mode are preferably set not to be saturated with the above dose. A dose to be applied in acquiring correction data is preferably at least 1 uR to several ten uR per frame from the viewpoint of correction accuracy.

In the above description, generally, the still image radiographic mode refers to radiography having a radiographic cycle (i.e., the X-ray irradiation cycle) of 1 sec or more. The moving image radiographic mode refers to radiography having a radiographic cycle of less than 1 sec, or radiography of irradiating a plurality of frames with X-rays continuously. As another definition, radiography having a period in which the power supply of the area sensor is OFF (set to the GND potential) between radiographic frames may be defined as still image radiography, and radiography having no OFF period may be defined as moving image radiography. As still another definition, radiography in which a maximum dose of 1 mR to several ten mR is applied to the surface of the area sensor may be defined as still image radiography, and radiography in which a maximum dose of 10 uR to several hundred uR is applied may be defined as moving image radiography.

This embodiment is exemplified by a case wherein the area sensor is formed using amorphous silicon p-i-n photodiodes as the conversion elements. However, in place of the amorphous silicon p-i-n photodiodes, amorphous silicon MIS conversion elements (MIS sensors) may be used. It is preferable to use cesium-iodide- or gadolinium-based phosphors to convert the X-rays into visible light. As the material of the conversion elements, other semiconductor materials (crystalline silicon, gallium arsenide, amorphous selenium, lead iodide, or mercury iodide) can be used.

This embodiment is exemplified by a case wherein the radiographic mode includes two modes, i.e., the "moving image radiographic mode" and "still image radiographic mode". However, the radiographic mode is not limited to these two types. Three or more types of radiographic modes may be prepared, and a plurality of (three or more types of) gain correction signals respectively corresponding to the three or more types of radiographic modes may be switched.

This embodiment is exemplified by an X-ray imaging apparatus which radiates X-rays and radiographs an object. However, the present invention is not limited to an apparatus which radiates X-rays and radiographs an object. Even an apparatus which outputs radiation other than X-rays and radiographs an object can obviously employ the scheme of this embodiment.

Second Embodiment

The second preferred embodiment of the present invention will be described.

FIG. 6 is a view of the second preferred embodiment of the present invention to show an example of the structure of a radiographic system which uses the X-ray imaging apparatus according to the first embodiment described above.

Referring to FIG. 6, an image processor 6070 is provided with the gain correcting function described above. According to the characteristic feature of the radiographic system of the second embodiment, an X-ray generating device which irradiates the target with X-rays is provided, and a control unit 103 for the image processor 6070 can control the operation of the X-ray generating device.

For example, the image processor 6070 has a microcomputer including a CPU which controls the overall X-ray imaging apparatus, a ROM which stores a control program or the like to be executed by the CPU, a work area necessary when the CPU runs the control program, and an EEPROM which serves as an offset memory 703, first gain correction memory 101, second gain correction memory 102, and the like. An imaging unit 104 is provided to an image sensor 6040. An output unit 706 is provided to, e.g., a display 6080.

The operation of this radiographic system will be described. X-rays 6060 generated by an X-ray tube 6050 serving as an X-ray generation source are transmitted through the patient or an observation portion 6062 such as the chest of a target object 6061 and enter the image sensor 6040. The entering X-rays contain information on the interior of the target object 6061. The image sensor 6040 obtains electric information which corresponds to the entering X-rays. The information is converted into a digital signal and image-processed by an image processor 6070 so that it can be monitored on the display 6080 in the control room.

The information of an image processed in this manner can be transferred to a remote place through a transmitting unit such as a telephone line or radio waves 6090, and displayed on a display 6081 or output to a film, so that a doctor at the remote place, e.g., a doctor room, which is different from the control room can make a diagnosis. The information obtained in the doctor room can be stored or saved on a storage medium using various types of storage materials, e.g., an optical disk, magneto-optical disk, or magnetic disk, or a storage medium 6110 such as a film or paper by a storage unit 6100 such as a film processor.

This embodiment is exemplified by an image correction unit provided in an image processor. However, the present invention is not limited to this, and an image correction unit may be provided in a radiographic unit. An image correction unit may be formed from an integrated circuit and incorporated in a reading device. A control unit may be arranged in a radiographic unit as well. The respective units may be connected or controlled through or without a wire. Furthermore, it is more preferable to form at least one of a gate driving device, reading device, correction unit, and control unit on an insulating substrate using materials such as polysilicon when reducing the size of an apparatus.

Third Embodiment

The third preferred embodiment of the present invention will be described.

Figure 11:
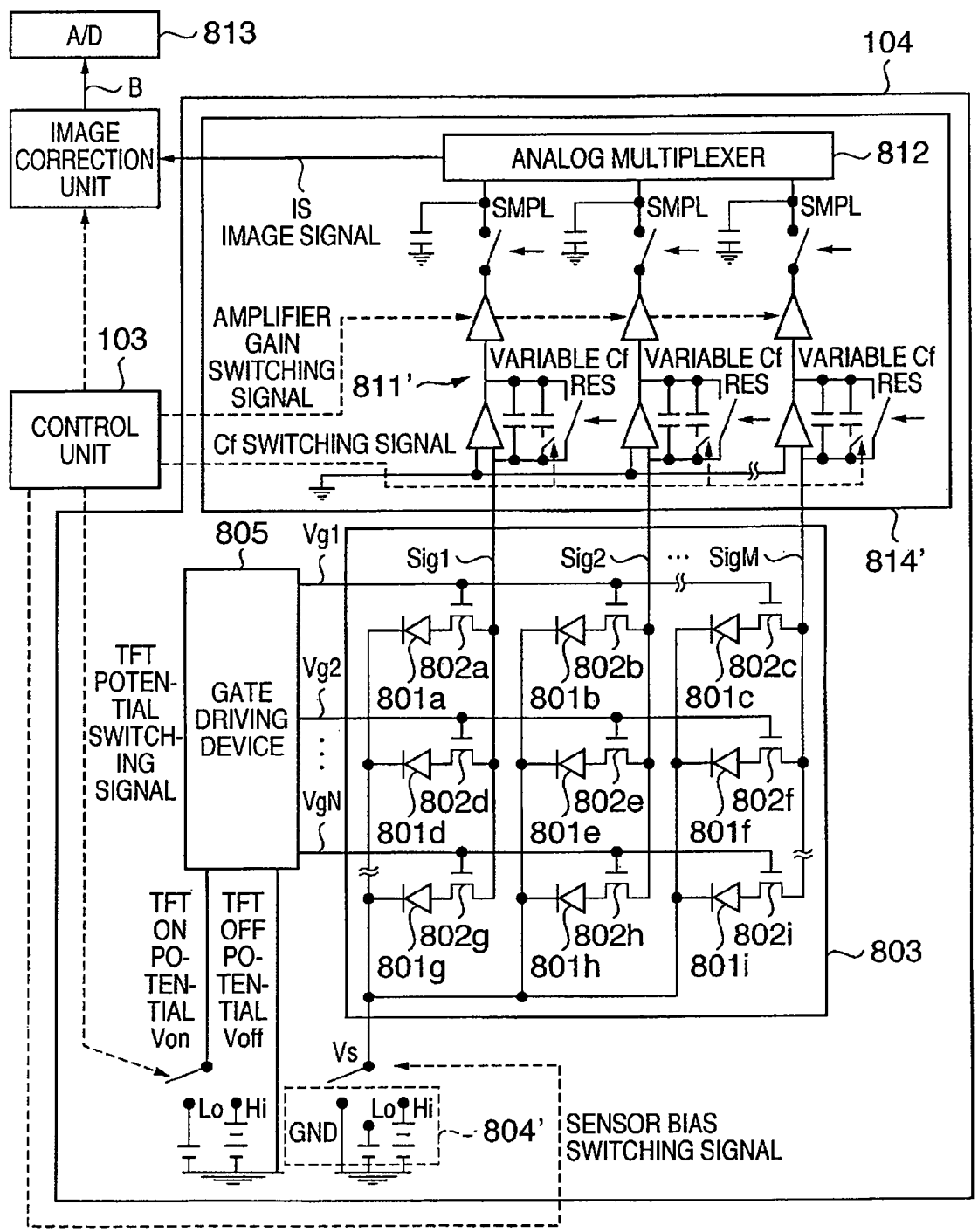
FIG. 11 is a circuit diagram of the third preferred embodiment of the present invention, schematically showing an example of the structure of an imaging unit which is included in an X-ray imaging apparatus.

FIG. 11 is a circuit diagram of the third preferred embodiment of the present invention, schematically showing an example of the structure of an imaging unit which is included in an X-ray imaging apparatus. Compared to FIG. 2 showing the first embodiment, the third embodiment differs in that an image correction unit is provided between an analog multiplexer 812 and A/D converter 813 of a reading device 814' and the correction process described above is executed in an analog mode. An arithmetic process of the image correction unit may be executed by combining an operational amplifier. An analog memory combined with a capacitor or the like may be used as a memory means. The contents of a digital memory may be D/A-converted and operated in an analog mode. Other basic operations and definitions are same as those of the first embodiment described with reference to FIGS. 1 to 5, and a detailed description will be omitted.

Fourth Embodiment

The fourth preferred embodiment of the present invention will be described.

Figure 12:
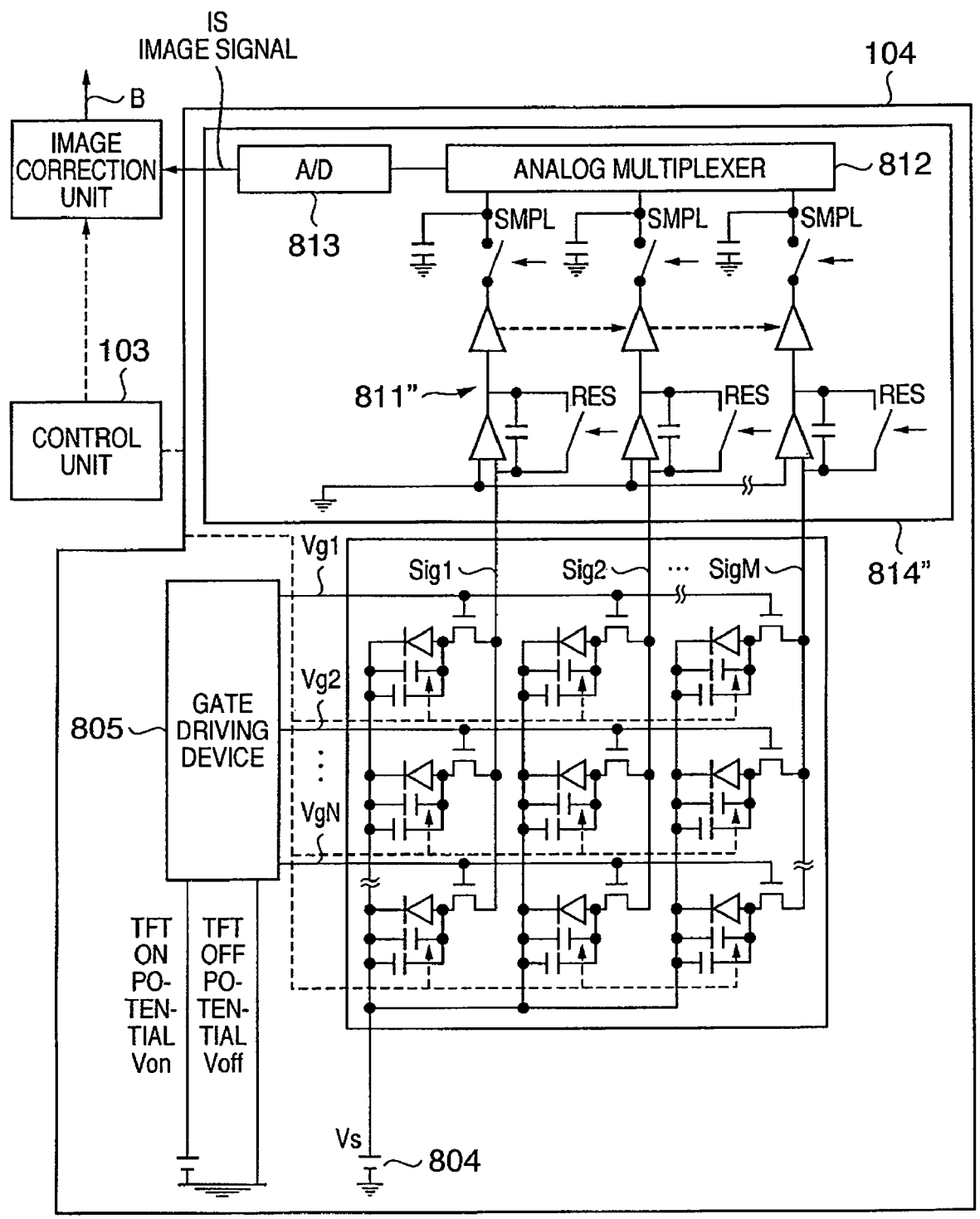
FIG. 12 is a circuit diagram of the fourth preferred embodiment of the present invention, schematically showing an example of the structure of an imaging unit which is included in an X-ray imaging apparatus.

FIG. 12 is a circuit diagram of the fourth preferred embodiment of the present invention, schematically showing an example of the structure of an imaging unit which is included in an X-ray imaging apparatus. Compared to FIG. 2 showing the first embodiment, the fourth embodiment differs in that a control unit 103 can switch the capacitance of a conversion element in accordance with moving image radiographic mode/still image radiographic mode. Accordingly, a reading device 814" uses a general gain amplifier 811". However, the reading device 814 in FIG. 8 or the reading device 814' in FIG. 2 may be used in place of the reading device 814". Other basis operations and definitions are same as those of the first embodiment described with reference to FIGS. 1 to 5, and a detailed description will be omitted. As described above, a dose is greatly different between moving image radiography and still image radiography. For this reason, it is desirable to control the capacitance of a conversion element to become small in the moving image radiographic mode and to become large in the still image radiographic mode from the viewpoint of saturation of the conversion element. The control unit 103 can more preferably switch the capacitance of the conversion element between the moving image radiographic mode and still image radiographic mode from the viewpoint of a dynamic range.

Other Preferred Embodiments of Present Invention

An arrangement is available in which the program code of software which implements the function of each embodiment described above is supplied to a computer in an apparatus or system which is connected to various types of devices to operate them, so that the function of each embodiment described above can be implemented. The various types of devices are operated in accordance with a program stored in the computer (CPU or MPU) of the system or apparatus, thus practicing the present invention. This arrangement is also incorporated in the scope of the present invention.

In this case, the program code itself of the software implements the function of each embodiment described above. The program code itself, and a means for supplying the program code to the computer, e.g., a storage medium which stores the program code, constitute the present invention. As the storage medium which stores such a program code, for example, a flexible disk, hard disk, optical disk, magneto-optical disk, CD-ROM, magnetic tape, nonvolatile memory card, ROM, or the like can be used.

When the computer performs the program code supplied to it, the function of each embodiment described above is implemented. Moreover, assume a case wherein the program code cooperates with an OS (operating system) or another application software which runs in the computer to implement the function of each embodiment described above. In this case, the program code is obviously incorporated in this embodiment of the present invention.

Assume a case wherein the supplied program code is stored in a memory which is provided to the function expansion board of the computer or a function expansion unit connected to the computer. Thereafter, a CPU or the like provided to the function expansion board or function expansion unit performs the actual process partly or entirely on the basis of the instruction of the program code, to implement the function of each embodiment described above. This case is also obviously incorporated in the present invention.

INDUSTRIAL APPLICABILITY

The present invention is used in an imaging apparatus, radiographic imaging apparatus, and radiographic system used for a medical diagnostic device, nondestructive inspection device, and the like.

As many apparently widely different embodiments of the present invention can be made without departing from the spirit and scope thereof, it is to be understood that the invention is not limited to the specific embodiments thereof except as defined in the claims.

CLAIM OF PRIORITY

This application claims priority from Japanese Patent Application No. 2004-231446 filed on Aug. 6, 2004 and Japanese Patent Application No. 2005-226622 filed on Aug. 4, 2005, which are hereby incorporated by reference herein.

The invention claimed is:

1. An imaging apparatus comprising:
  an imaging unit having a plurality of conversion elements, said imaging unit being configured to obtain an image signal according to a radiation dose transmitted through an object; and
  a gain correction unit which corrects, in order to correct gain characteristics of the plurality of conversion elements, an image signal from said imaging unit using a correction signal stored on a storage medium, the gain characteristics being input/output characteristics of each of the plurality of conversion elements, the input/output characteristics being a relation between the number of photons or radiation dose incident on each of the plurality of conversion elements and charge amount or output signal amount generated in each of the plurality of conversion elements according to the number of photons or radiation dose, the correction signal being a signal obtained from said imaging unit by a radiation irradiation on said imaging unit without an object between a radiation generating device and said imaging unit,
  wherein said gain correction unit is arranged to select a correction signal corresponding to a radiographic mode from a plurality of correction signals corresponding to a plurality of radiographic modes between which a radiation dose to said imaging unit in order to obtain the image signal for one image differs, and correct the image signal in the radiographic mode by performing division for the image signal and the selected correction signal.

2. The apparatus according to claim 1, wherein the plurality of radiographic modes include a moving image radiographic mode and still image radiographic mode, a radiation dose to said imaging unit in order to obtain the image signal for one image differs between the moving image radiographic mode and the still image radiographic mode, and
  said gain correction unit corrects the image signal from said imaging unit using a first correction signal selected from the plurality of correction signals in the moving image radiographic mode, and using a second correction signal selected from the plurality of correction signals in the still image radiographic mode.

3. The apparatus according to claim 2, further comprising a plurality of said storage mediums to store the correction signals for one image.

4. The apparatus according to claim 2, further comprising a control unit which selects the correction signal from the plurality of correction signals in accordance with the plurality of radiographic modes,
  wherein said gain correction unit corrects the image signal using the correction signal selected from the plurality of correction signals by said control unit.

5. The apparatus according to claim 4, wherein
  said control unit partly or entirely turns off power supplies, which serve to cause said imaging unit to output the image signal, for each reception of the image signal for one image in the still image radiographic mode of the plurality of radiographic modes.

6. The apparatus according to claim 4, wherein
  said control unit updates at least one of the plurality of correction signals corresponding to the plurality of radiographic modes.

7. The apparatus according to claim 1, wherein
  each of said plurality of conversion elements has a photoelectric conversion element, and
  said photoelectric conversion element comprises one of a p-i-n photodiode and MIS sensor formed using amorphous silicon.

8. The apparatus according to claim 1, wherein
  each of said plurality of conversion elements is a device which converts the radiation into charges directly and is formed using any one semiconductor material selected from the group consisting of crystalline silicon, gallium arsenide, amorphous selenium, lead iodide, and mercury iodide.

9. An imaging system comprising:
  an imaging apparatus which has an imaging unit including a plurality of conversion elements, said imaging unit being configured to obtain an image signal according to a radiation dose transmitted through an object; and
  a gain correction unit which corrects, in order to correct gain characteristics of said conversion elements, an image signal from said imaging apparatus using a correction signal stored on a storage medium, the gain characteristics being input/output characteristics of each of the plurality of conversion elements, the input/output characteristics being a relation between the number of photons or radiation dose incident on each of the plurality of conversion elements and charge amount or output signal amount generated in each of the plurality of conversion elements according to the number of photons or radiation dose, the correction signal being a signal obtained from said imaging unit by a radiation irradiation on said imaging unit without an object between a radiation generating device and said imaging unit,
  wherein said gain correction unit is arranged to select a correction signal corresponding to a radiographic mode from a plurality of correction signals corresponding to a plurality of radiographic modes between which a radia- 10. An imaging apparatus comprising:
an imaging unit having a plurality of conversion elements, said imaging unit being configured to obtain an image signal according to a radiation dose transmitted through an object; and
a gain correction unit which corrects, in order to correct gain characteristics of the plurality of conversion elements, an image signal from said imaging unit using a correction signal stored on a storage medium, the gain characteristics being input/output characteristics of each of the plurality of conversion elements, the input/output characteristics being a relation between the number of photons or radiation dose incident on each of the plurality of conversion elements and charge amount or output signal amount generated in each of the plurality of conversion elements according to the number of photons or radiation dose, the correction signal being a signal obtained from said imaging unit by a radiation irradiation on said imaging unit without an object between a radiation generating device and said imaging unit,
wherein said gain correction unit is arranged to select a correction signal corresponding to a radiation dose incident on said imaging unit from a plurality of correction signals corresponding to a plurality of radiographic modes between which a radiation dose to said imaging unit in order to obtain the image signal for the image differs, and correct the image signal under the radiation dose by performing division for the image signal and the selected correction signal in accordance with a radiation dose to said imaging unit in order to obtain the image signal for one image.

11. An imaging system comprising:
an imaging apparatus which has an imaging unit including a plurality of conversion elements, said imaging unit being configured to obtain an image signal according to a radiation dose transmitted through an object; and
a gain correction unit which corrects, in order to correct gain characteristics of said conversion elements, an image signal from said imaging apparatus using a correction signal stored on a storage medium, the gain characteristics being input/output characteristics of each of the plurality of conversion elements, the input/output characteristics being a relation between the number of photons or radiation dose incident on each of the plurality of conversion elements and charge amount or output signal amount generated in each of the plurality of conversion elements according to the number of photons or radiation dose, the correction signal being a signal obtained from said imaging unit by a radiation irradiation on said imaging unit without an object between a radiation generating device and said imaging unit,
wherein said gain correction unit is arranged to select a correction signal corresponding to a radiation dose incident on said imaging unit from a plurality of correction signals corresponding to a plurality of radiographic modes between which a radiation dose to said imaging unit in order to obtain the image signal for one image differs, and correct the image signal under the radiation dose by performing division for the image signal and the selected correction signal in order to obtain the image signal for one image.

12. An imaging method comprising:
an imaging step of capturing an image of an object according to a radiation dose transmitted through the object by an imaging unit having a plurality of conversion elements; and
a gain correction step of correcting, in order to correct gain characteristics of said conversion elements, an image signal of the object which is captured in the imaging step using a correction signal stored on a storage medium, the gain characteristics being input/output characteristics of each of the plurality of conversion elements, the input/output characteristics being a relation between the number of photons or radiation dose incident on each of the plurality of conversion elements and charge amount or output signal amount generated in each of the plurality of conversion elements according to the number of photons or radiation dose, the correction signal being a signal obtained from said imaging unit by a radiation irradiation on said imaging unit without an object between a radiation generating device and said imaging unit,
wherein in the gain correction step, a correction signal corresponding to a radiographic mode is selected from a plurality of correction signals corresponding to a plurality of radiographic modes between which a radiation dose to said imaging unit in order to obtain the image signal for one image differs, and the image signal is corrected by performing division for the image signal and the selected correction signal in accordance with a plurality of radiographic modes.

13. A computer-readable storage medium storing a computer program for causing a computer
to perform a selection of a correction signal corresponding to a radiographic mode from a plurality of correction signals, which is stored in the computer-readable storage medium, corresponding to a plurality of radiographic modes between which a radiation dose to an imaging unit in order to obtain the image signal for one image differs, and
to perform a correction of an image signal of an object according to a radiation dose transmitted through the object, which is captured by an imaging unit so as to correct gain characteristics of a plurality of conversion elements arranged in said imaging unit in the radiographic mode by performing division for the image signal and the selected correction signal in the radiographic mode, the gain characteristics being input/output characteristics of each of the plurality of conversion elements, the input/output characteristics being a relation between the number of photons or radiation dose incident on each of the plurality of conversion elements and charge amount or output signal amount generated in each of the plurality of conversion elements according to the number of photons or radiation dose, the correction signal being a signal obtained from said imaging unit by a radiation irradiation on said imaging unit without an object between said radiation generating device and said imaging unit.

14. A computer-readable storage medium storing a computer program for causing a computer
to perform a selection of a correction signal corresponding to a radiation dose incident on an imaging unit from a plurality of correction signals, which is stored in the computer-readable storage medium, corresponding to a plurality of radiographic modes between which a radiation dose to said imaging unit in order to obtain the image signal for one image differs, and to perform a correction of an image signal of an object according to a radiation dose transmitted through the object, which is captured by an imaging so as to correct gain characteristics of a plurality of conversion elements arranged in said imaging unit under the radiation dose by performing division for the image signal and the selected correction signal in order to obtain the image signal for one image, the gain characteristics being input/output characteristics of each of the plurality of conversion elements, the input/output characteristics being a relation between the number of photons or radiation dose incident on each of the plurality of conversion elements and charge amount or output signal amount generated in each of the plurality of conversion elements according to the number of photons or radiation dose, the correction signal being a signal obtained from said imaging unit by a radiation irradiation on said imaging unit without an object between said radiation generating device and said imaging unit.

15. The apparatus according to claim 1, wherein the gain characteristics include at least one of sensitivity specific to each of the plurality of conversion elements and gamma.

* * * * *